United States Patent [19]

Mikos

[11] Patent Number: 5,522,895
[45] Date of Patent: Jun. 4, 1996

[54] BIODEGRADABLE BONE TEMPLATES

[75] Inventor: Antonios G. Mikos, Houston, Tex.

[73] Assignee: Rice University, Houston, Tex.

[21] Appl. No.: 96,780

[22] Filed: Jul. 23, 1993

[51] Int. Cl.$^6$ .................................................. A61F 2/28
[52] U.S. Cl. .............................. 623/16; 623/11; 606/76; 606/77
[58] Field of Search ......................... 623/11, 16; 606/70, 606/71, 76, 77

[56] References Cited

U.S. PATENT DOCUMENTS

| | | |
|---|---|---|
| 4,485,097 | 11/1984 | Bell . |
| 4,553,272 | 11/1985 | Mears . |
| 4,655,777 | 4/1987 | Dunn et al. ............................. 623/16 |
| 4,661,536 | 4/1987 | Dorman et al. ......................... 623/16 |
| 4,843,112 | 6/1989 | Gerhart et al. ......................... 623/16 |
| 5,041,138 | 8/1991 | Vacanti . |
| 5,292,349 | 3/1994 | Foresti .................................... 623/16 |
| 5,308,623 | 5/1994 | Fues et al. ............................... 623/16 |

FOREIGN PATENT DOCUMENTS 2215209  9/1989  United Kingdom ..................... 606/77

OTHER PUBLICATIONS

Cima, L. G., *Biotehn. Bioeng.*, 38:145–158, 1991.
Cima, L. G., *J. Biomech. Eng.*, 113:143–151, 1991.
Chu, C., *Polymer*, 26:591–594, 1985.
Davies, J., *Scanning Microscopy*, 2:1445–1452, 1988.
Ecarot-Charrier, *Endocrinol.*, 123:768–773, 1988.
Freed, L. E., *J. Biomed. Mater. Res.*, 27:11–23, 1993.
Gerhart, T. N., *J. Biomed. Mater. Res.*, 22:1071–1082, 1988.
Gerhart, T. N., *J. Biomed. Mater. Res.*, 23:1–16, 1989.
Holland, S., *J. Controlled Release*, 4:155–180, 1986.
Ishaug, S. L., *Biomaterials for Drug and Cell Delivery*, MRS Symposium Proceedings, vol. 331, Materials Research Society, Pittsburgh, in press (1993).
Langer, R., *Science*, 260:920–926, 1993.
Leenslag, J. W., *Biomaterials*, 8:70–73, 1987.
Mikos, A. G., *J. Biomed. Mater. Res.*, 27:183–189, 1993.
Mikos, A. G., *Abstr. AIChE Meeting*, Abstract 15e, Nov. 1991.
Mikos, A. G., *Biomaterials*, 14:323–330, 1993.
Mikos, A. G., *Biotechn. Bioeng.*, 42:716–723, 1993.
Mikos, A. G., *Abstr. AIChE Meeting*, Abstract 3f (Nov. 1991).
Miller, R., *J. Biomed. Mater. Res.*, 11:711–719, 1977.
Moskalweski, *Am. J. Anat.*, 167:249, 1983.
Puleo, O. A., *J. Biomed. Mater. Res.*, 25:711–723, 1991.
Rodier, *Cancer*, 68:2545–2549, 1991.
Saha, S., *J. Biomed. Mater. Res.*, 18:435–462, 1984.
Stein, E., *Abstr. AIChE Meeting*, Abstract 3g (Nov. 1991).
Thomson, *Biomaterials for Drug and Cell Delivery*, MRS Symposium Proceedings, vol. 331, Materials Research Society, Pittsburgh, in press (1993).
Uyama, S., *Polym. Mater. Sci. Eng. Prepr.*, 66:182–183, 1992.
Vacanti, C. A., *Plast. Reconstr. Surg.*, 88:753–759, 1991.
Vacanti, C. A., *Abstr. AIChE Meeting*, Abstract 3i (Nov. 1991).
Vacanti, C. A., *Arch. Surg.*, 123:545–549, 1988.
Vacanti, C. A., *J. Pediatr. Surg.*, 23:3–9, 1988.
Wald, H. L., *Chondrocyte Culture on Diodegradable Polymer Substrates*, M. S. Thesis, Dept. of Chem. Eng. M.I.T., 1992.
Wald, H. L., *Biomaterials*, 14:270–278, 1993.
Wang, H. T., *Biomaterials*, 11:679–685, 1990.
Witschger, P. M., *J. Orthop. Res.*, 9:48–53, 1993.
Yannas, V., "Regeneration of Skin and Nerve by Use of Collagen Templates," in Collagen III, M. E. Nimni (Ed.), CRC Press, Boca Raton, 1988, pp. 87–116.

*Primary Examiner*—Paul B. Prebilic
*Attorney, Agent, or Firm*—Pravel, Hewitt, Kimball & Krieger

[57] ABSTRACT

A biodegradable, bioresorbable, three-dimensional template for repair and replacement of diseased or injured bone which provides mechanical strength to bone while also providing a guide for growth of bone tissue. Preferably, the template is formed of biodegradable materials, for example, poly(L-lactic acid), poly(D, L-lactic acid), poly (D, L-lactic-co-glycolic acid), poly (glycolic acid), poly (ε-caprolactone), polyortho esters, and polyanhydrides, and has the capacity of being rendered porous, either in vitro or in vivo. A pore-forming component, which may or may not be a polymeric material, is mixed within a continuous matrix formed of a biodegradable material, the pore-forming component having a rate of degradation which exceeds that of the matrix. Differential dissolution or biodegradation provides porosity to the template.

2 Claims, No Drawings

BIODEGRADABLE BONE TEMPLATES

FIELD OF THE INVENTION

This invention relates to prosthetic templates providing mechanical strength and support for growth of normal tissues in the treatment of injured bone. More particularly, this invention provides a biodegradable, three dimensional template for replacement or repair of diseased or injured bone, the template providing mechanical support for surrounding bone while also providing a guide for ingrowth of bone tissue into the template.

BACKGROUND OF THE INVENTION

In the treatment, repair, or reconstruction of injured or damaged bone, foreign materials are often implanted in the body in the form of prostheses, bone pins, bone cement, and the like. For many reasons, it would be highly desirable if these foreign materials could be eliminated and replaced by natural tissues as the body repairs the injured area.

Biodegradable and bioresorbable materials have been examined for use as implantable prostheses, and the like, and also as templates around which the body can regenerate various types of soft tissue. During or after soft tissue regeneration is complete, the biodegradable template is naturally eliminated from the body.

It would be highly desirable to develop a biodegradable material having sufficient load bearing properties to permit its use as a bone substitute as well as a bone template so that natural bone tissue regenerates in the prosthetic template while the template degrades and is gradually eliminated from the body to be replaced by natural bone tissue.

SUMMARY OF THE INVENTION

It has been found that biodegradable materials can be fabricated into three dimensional anatomical shapes having load bearing properties similar to or exceeding that of natural bone. An implant fabricated of the biodegradable material has the capability of being rendered porous and can serve as a prosthetic template implant fostering ingrowth of new bone tissue. The template can be implanted without first being rendered to its porous state. Porosity can be achieved after implantation by a faster rate of biodegradation of a pore forming component of the implant relative to a slower rate of degradation of a continuous or matrix component of the implant. Alternatively, the implant may be rendered partially or wholly porous prior to implantation by partially or wholly removing the pore-forming component from the matrix component of the implant. In either embodiment, the implant has sufficient compressive strength and modulus to serve as a bone replacement prosthesis during that period wherein the body regenerates new natural bone within and to the shape of the implant. Ultimately, the implant is replaced by natural bone as the implant biodegrades and by such process is displaced or eliminated from the body by natural processes.

Upon initial implantation, the biodegradable porous implant serves as a supportive prosthesis, replacing damaged bone area and providing mechanical support. The implant also provides a template for ingrowth of natural bone and regeneration of bone, particularly into the porous areas of the prosthetic template. In one embodiment, the implant is seeded with osteoblasts prior to implantation to provide regeneration sites for bone tissue. Bone cell growth, formation of bone nodules, and secretion of bone matrix by the seeded bone cells adds to the strength of the implant and to the rapid replacement with natural bone. The rate at which the biodegradable and bioresorbable prosthetic template degrades or absorbs can be matched to the rate at which the natural bone regenerates within and into the prosthetic template. Upon elimination of the template from the body, it will then have been replaced by new bone.

DESCRIPTION OF THE INVENTION

The prosthetic templates of the present invention are biodegradable to products which either enter metabolic pathways and are thereby eliminated from the body (bioresorbed) or are eliminated from the body by other natural processes (e.g. in the urine). The templates preferably have a three-dimensional, anatomical shape conforming to the desired bone to be replaced. The biodegradable templates are fabricated of polymers and by methods which result in implants which are capable of being rendered porous for tissue ingrowth while retaining sufficient mechanical strength to be suitable for replacement of load bearing bones. For example, in their preporous state the templates of the present invention possess a compressive strength of approximately 5 MPa to 50 MPa and a compressive modulus of approximately 50 MPa to 500 MPa as tested by an Instron Materials Testing Machine according to American Society for Testing and Materials (ASTM) Standard F451-86. The values of 5 MPa compressive strength and 50 MPa compressive modulus correspond to the mid-range values for human trabecular bone.

The desired strength of the template will vary with the bone to be treated, e.g., load-bearing or not. The templates of the present invention have a high ultimate porosity capacity, resulting in a highly porous matrix containing a uniformly distributed and interconnected pore structure. Pore volume of the templates is approximately 20% to 50%, and the average pore diameter is approximately 50 to 250 µm. The pore volume and diameter also directly relate to the rate of tissue ingrowth and template degradation. The porous template of the present invention accommodates large number of cells adhering to the template, permits cells to be easily distributed throughout the template, and allows an organized network of tissue constituents to be formed. The template preferably promotes cell adhesion and permits the attached cells to retain differentiated cell function.

The prosthetic template comprises at least two components, a continuous matrix component and an included pore-forming component. The matrix component comprises a biodegradable material having a rate of degradation which at least matches the rate at which the body regenerates natural bone tissue. The pore-forming component is a material which differs from the matrix material such that it may be differentiated from the matrix component and ultimately be removed therefrom by differential dissolution or biodegradation to provide porosity to the prosthetic template either prior to or after implantation.

The biodegradable, bioresorbable prosthetic templates of the present invention preferably are formed of polymeric materials, the matrix polymer having a rate of degradation which is matched to the rate of tissue in-growth. The matrix polymeric substance preferably ranges in weight average molecular weight from approximately 50,000 to 200,000. Crystallinity of the matrix polymer of implant is approximately 0 to 25%. The molecular weight and molecular weight distribution of the matrix polymer of the template is related to the rate at which the template biodegrades. In a template having a matrix polymer of broad molecular weight distribution, e.g., having a polydispersity index (Mw/Mn) greater than 2 fractions of the material exist in short to long polymeric chains. This diversity allows a continuation of degradation over time without sharp changes, e.g., in pH due to degradation products, as may occur with a material having a narrow molecular weight distribution. In the present invention, the polydispersity index of the matrix polymer is preferably in the range of 3–6.

Unless wholly removed from the matrix polymer of the implant before implantation, the molecular weight, molecular weight distribution and degree of crystallinity of the pore-forming polymer is also of significant concern. Generally, the pore-forming polymer should biodegrade and/or bioresorb at a rate which is at least four times greater than that of the matrix polymer. Further, the pore-forming polymer should have a polydispersity index of at least 3 to provide for a controlled degradation over a period of time that avoids intolerable localized pH concentrations due to its degradation by-products.

The template may optionally contain additional ingredients such as therapeutic agents incorporated into the matrix or the pore-forming polymer for time release as that polymer degrades. In a preferred embodiment, the template is seeded with osteoblasts prior to implantation to provide sites for promoted regeneration of bone tissue.

BIODEGRADABLE POLYMERS

Biodegradable polymers are known, commercially available, or can be synthesized using known and published methods. Examples of polymers useful in the present invention include poly(L-lactic acid), poly(D L-lactic acid), poly(D L-lactic-co-glycolic acid), poly(glycolic acid), poly(epsilon-caprolactone), polyorthoesters, and polyanhydrides. These polymers may be obtained in or prepared to the molecular weights and molecular weight distribution needed for service as either the matrix polymer or the pore-forming polymer by processes known in the art. Preferred polymers are poly(alpha-hydroxy esters). Suitable solvent systems are published in standard textbooks and publications. See, for example, *Lange's Handbook of Chemistry*, Thirteenth Edition, John A. Dean, (Ed.), McGraw-Hill Book Co., New York, 1985. These polymers may be formed into fibers and webs by standard processing techniques including melt extrusion and spin casting, and are commercially available in woven or non-woven form.

THREE-DIMENSIONAL SHAPING

Shape is integral to the function of bone prosthesis, therefore, the prosthetic templates of the present invention are preferably fabricated of materials and by methods which permit three-dimensional anatomical shaping. Three-dimensional shaping may be achieved by forming the template in an anatomically-shaped mold, by machining a block matrix into the desired shape, or by laminating polymeric membranes together to form the desired anatomical shape. Necessary crevices, curves, and the like may be added to the prosthetic templates by machining, or by cutting using known methods such as scissors, scalpel, laser beams, and the like.

POROSITY

The prosthetic templates of the present invention contain a high ultimate porosity capacity. That is, the templates are fabricated in a manner which results in an implant capable of being rendered highly porous prior to implantation. For example, the matrix may be formed around included particles or fibers which particles or fibers are subsequently removed from the matrix by solvent dissolution or other methods of degradation, leaving a highly porous matrix template structure. Alternatively, the particles or fibers embedded within the formed matrix may be retained in the template for dissolution or degradation in situ after implantation. In addition, portions of the pore-creating material may be removed prior to implantation of the template providing a range of actual to ultimate porosities of the implantable templates.

The ultimate porosity capacity may be defined as the percent porosity of the matrix after at least 90% of the pore forming material has been removed from the template, either in vitro or in vivo. In the present invention, it is preferred that the ultimate porosity capacity of the biodegradable/bioresorbable templates be in the range of 20% to 50% volume of the template.

OSTEOBLAST SEEDING

In a preferred embodiment, a prosthetic template of the present invention is seeded with osteoblasts prior to implantation. Donor osteoblast cells, preferably autologous, are harvested and cultured as described in Puleo et al., *J. Biomed. Mater. Res.*, 25:711–723, 1991, which is hereby incorporated by reference. The template may be prewetted, for example, ethanol and then medium. A suspension of osteoblasts in growth medium is seeded in the template, for example by placing drops of the cell suspension onto or into the prosthetic template and allowing the suspension to wick into the polymeric foam. After placing the cells on or in the template, the template may be implanted directly into a recipient or, preferably, the template may be placed in tissue culture for attachment. Preferably, the cells and template are incubated in culture medium in a tissue incubator at approximately 37° C. and 5% $CO_2$. The amount of time required for cell attachment and growth will vary with the template, its size, porosity, and with the desired percentage of replacement bone in the template prior to implantation. Generally, the incubation period will range from about 30 minutes to 24 hours for cell attachment, followed by approximately six hours to four weeks for cell growth and bone deposition in vitro. The longer the culture period, the greater the replacement of template material with natural bone tissue. As the transplanted cell population grows and the cells function normally, they will begin to secrete their own extra-cellular matrix for structural support. Concurrently, the continuously degrading polymer will be eliminated as the need for an artificial support diminishes. For example, after 21–30 days of culture, bone nodules form in the osteoblast-seeded implant. Calcium phosphate salts, collagen, and alkaline phosphatase may be analyzed as markers of bone matrix formation.

METHODS OF PREPARATION

The biodegradable prosthetic templates of the present invention which have the features described above, including high mechanical strength necessary for replacement of load bearing bones, high ultimate porosity capacity to permit ingrowth of new bone tissue, and a rate of degradation approximately matching the rate of new tissue growth may, for example, be formed by the methods described below. In its simplest embodiment, the templates of the present invention are formed by distributing within a polymeric matrix a pore creating substance. Regardless of the specific methods used to form the template, the product will include a three-dimensional, anatomically shaped prosthetic template having a high ultimate porosity capacity due to the presence of a pore creating substance dispersed within the matrix.

The pore creating substance may be formed for example of salts, polysaccharides, protein, polymers other than the matrix polymers, or other non-toxic materials such as gelatin which are, for example, soluble in a solvent which does not dissolve the matrix polymer; made fluid at a higher glass transition temperature (Tg) or melting temperature (Tm) than the matrix polymer; or otherwise differentiated from the matrix polymer so as to retain an independent structure from the polymeric matrix. When subsequently removed, the desired pores are formed within the matrix.

The temperature required to fluidize polymers is that which permits non-hindered flow of polymer chains. For amorphous polymers this "flow temperature" is the glass transition temperature (Tg). However, for semi-crystalline polymers this "flow temperature" is the melting temperature (Tm). As used herein, flow temperature is meant to be that temperature which permits non-hindered flow of polymer chains and includes, as appropriate, Tg for amorphous polymers and Tm for at least semi-crystalline polymers.

The pore creating substance may be in the form of particles such as salt, which after forming a matrix in which the particles have been included, the particles are leached out or otherwise removed from the matrix leaving a polymeric matrix with high porosity. The pore creating substance may be in the form of fibers such as polymeric fibers or webs dispersed within a formed polymeric matrix. The dispersed fibers and the surrounding matrix possess differential rates of degradation, with the fibers being degraded at a faster rate than the matrix, thereby being removed from the template and creating a highly porous polymeric template.

Biocompatible prosthetic templates may be prepared, for example, by pouring a polymer solution into an anatomically-shaped mold. To form the porous prosthesis, the mold may contain a pore-creating substance. Alternatively, the polymer solution being poured into the mold may include a dispersed pore-creating substance. Within the mold, the polymeric solution containing dispersed pore-creating substance is cured into a polymeric foam by methods known in the art, including evaporation of solvent, heat curing, or irradiation. Alternatively, the template may be formed by dispersing the pore-creating substance in a body of powdered polymer. Preferably, the pore-creating substance is a first polymer in fiber or web form dispersed in a body of powdered second polymer. The second polymer has a lower flow temperature (Tf) such that when the dispersion is heated above the flow temperature of the powder, the powder is fluid, but the dispersed fibers are not. The fluid polymer is next solidified, e.g., by permitting the dispersion to return to ambient temperature, resulting in a polymeric matrix having entrapped therein the pore-forming substance.

Once the polymeric matrix has formed about the pore-creating substance, the pore-creating substance may be removed from the matrix template. For example, fibers or particles may be dissolved out of the matrix by immersing the template in water or an appropriate solvent. Alternatively, enzymes or chemical agents may be used to remove the pore-creating substance.

In a preferred embodiment, a first polymer is used to form the template matrix and a second polymer is used to form the pore-creating substance dispersed within the first polymer. Both first and second polymers are biodegradable but the second degrades at a faster rate than the first polymer, e.g., approximately two to eight times faster, and preferably about four times faster creating the desired porous template matrix for ingrowth and proliferation of cells. For example, poly(glycolic acid) (PGA) fiber meshes may be dispersed within poly(L-lactic acid) (PLLA). Upon curing of the PLLA matrix, the PGA fiber mesh is embedded within the PLLA matrix. The PGA fibers biodegrade at a more rapid rate than PLLA, thus creating a template having a high ultimate porosity capacity.

The pore creating substance may be formed of a low molecular weight polymer while the matrix is formed of a high molecular weight polymer. Because the low molecular weight polymers degrade at a faster rate than the high molecular weight polymers an implant having a desired rate of degradation of each of the pore creating substance and the matrix can be formed.

Shaping of the Template

The biodegradable prosthetic templates formed as described above may be prepared in molds having the desired three-dimensional shape. The formed polymeric matrix may then be machined and/or modified by methods known in the art to form the precise contours and shapings required. Alternatively, a block matrix polymer may be formed as described above and then machined and/or otherwise cut to the desired shape by known methods. Crevices, smoothing, and other adjustments to the shaped anatomic prosthesis may be performed, for example by machining tools, knives, scissors, laser beams and the like.

It is also possible to form the three-dimensional anatomical prosthesis by laminating together two or more prosthetic templates formed as described above to create the desired three-dimensional anatomically-shaped prosthesis as desired.

PREIMPLANTATION TREATMENTS

The template may be directly implanted or may be further treated to induce porosity and to add additional beneficial agents. In a preferred embodiment the template is treated to induce porosity by dissolving the pore-forming material in a solvent which does not dissolve the matrix polymer.

Alternatively, in vivo degradation of the pore-creating substance at a faster rate than the template matrix, such as PGA fibers which degrade within months of implantation in a PLLA matrix which may take more than one year to degrade, permits gradual replacement of the pore-creating substance with growing bone cells. The resorbing pore-creating substance is gradually replaced with newly formed bone tissue, maintaining a mechanically strong bone prosthesis. The more slowly degrading polymeric matrix is then resorbed and replaced with bone tissue proliferating from the network of growing tissue already present throughout the prosthetic template.

THERAPEUTIC AGENTS

In an alternative embodiment, therapeutic agents may be incorporated into the polymeric matrix or into the pore-creating substance for timed release of these agents in situ. Agents such as growth factors, antibiotics, immune stimulators, immune suppressants, and the like may be incorporated into the polymeric matrix or the pore-creating substance, and are slowly released as the matrix is degraded.

IMPLANTATION

The biodegradable, bioresorbable prosthetic templates of the present invention are implanted in desired sites in bone.

As described above, the templates may be implanted as a shaped polymeric prosthesis containing a pore-creating substance having an ultimate porosity capability for ingrowth of new bone tissue. The pore-creating substance may be removed in vivo, or alternatively, the template may be pretreated prior to implantation to partially or totally remove the pore-creating substance. The template is implanted for in situ ingrowth of bone tissue at the site of implantation. In a preferred embodiment, the template is seeded with osteoblast cells prior to implantation, and may be cultured to permit initial growth and deposition of bone matrix in vitro, providing for implantation a template containing growing viable sites of bone tissue as described above.

EXAMPLE 1

PREPARATION OF PLGA/GELATIN COMPOSITE AND PLGA FOAM

Three main stages are required for the production of the PLGA foam. These include:

1. The manufacture of gelatin microspheres;
2. The formation of a composite material consisting of gelatin microspheres surrounded by a PLGA matrix; and
3. The removal of the gelatin.

A. Manufacture of Gelatin Microspheres

Porcine skin gelatin (20 g) (Sigma Chemical Company, St. Louis Mo.) was dissolved in 100 ml of distilled, deionized water maintained at 50° C. in a water bath. The solution was stirred continuously, using a magnetic stirrer, for approximately 30 minutes until all the gelatin had dissolved. Toluene (730 ml) and chloroform (230 ml) were added to a four liter baffled beaker to which 20 ml of a surfactant Arlacel 83 (Sigma) was added. The solution was mixed continuously using a propeller stirrer as the 100 ml of gelatin solution was slowly added using a 10 ml pipette. After ten minutes, the stirrer and baffles were removed and the gelatin microspheres produced were separated from the solution using a fine mesh sieve (53 μm). The gelatin microspheres were then washed in 100 ml of chloroform and allowed to dry in a fume hood for 24 hours and then in a lyophilizer for 24 hours. The dried microspheres were ground gently using a mortar and pestle in order to break up any aggregates and then sieved into the following size ranges: 53–250 μm; 250–500 μm; 500–1000 μm; greater than 1000 μm. The separated microspheres were then stored in a vacuum desiccator until needed.

B. Formation of PLGA/Gelatin Composite

A composite material consisting of gelatin microspheres embedded in a poly(DL-lactic-co-glycolic acid) (PLGA) matrix was formed by the following procedure. Several grams of PLGA 50:50 (Medisorb, Cincinnati, Ohio) were ground into a fine powder using a micro-mill for approximately 20 minutes. (The ratio 50:50 stands for the copolymer ratio of lactic acid to glycolic acid.) The ground PLGA (0.04 g) was mixed with 0.04 g of gelatin microspheres in the size range of 250–500 μm. This combination is calculated to yield a final foam having approximately 50% porosity once the gelatin is removed. This mixture was then poured into a cylindrical Teflon mold, 6 mm in diameter. The mold was then closed and moderate pressure, e.g., between finger and thumb, was applied to compress the PLGA/gelatin mixture. The approximate height of the cylindrical mold was 4–5 mm. The mold was then placed in a convection oven at 80° C. for 70 minutes. (PLGA Tg=50°–60° C.). The mold was then cooled at 25° C., and its contents removed for microscopic examination. Inspection by light microscopy and by scanning electron microscopy indicated the PLGA had molded about the gelatin microspheres and had formed a structurally intact composite.

C. Removal of Gelatin Microspheres

To prepare the PLGA foam, the gelatin microspheres were removed from the matrix by the following leaching method: the PLGA/gelatin composite was placed in 15 ml of distilled, deionized water at 37° C. under agitation for 20 hours. The water was then removed and replaced with fresh distilled deionized water. After further agitation for four hours, the PLGA foam was removed and dried in a lyophilizer for 24 hours. Analysis by light microscopy and scanning electron microscopy indicated the gelatin beads had been leached out leaving an intact, highly porous, PLGA foam.

EXAMPLE 2

PREPARATION OF ADDITIONAL PLGA/GELATIN COMPOSITES AND PLGA FOAMS

The procedure described for Example 1 was repeated, except that gelatin microspheres in a size range of 53–250 μm were utilized to form an intact, highly porous, PLGA foam having a smaller pore size than described for Example 1. In a similar fashion, the procedure of Example 1 was followed except that gelatin microspheres in the size range of 500–1000 μm were used to generate and intact, highly porous foam having a larger pore size than the foam described for Example 1.

The procedure described in Example 1 was repeated except that PLGA 85:15 (Medisorb) was utilized to form an intact, high porous PLGA foam which degrades more slowly than that described for Example 1.

The procedure described for Example 1 was followed except that PLGA 70:30 (Polysciences, Warrington, Pa.) was used, resulting in a polymer foam which degrades more slowly than that described for Example 1.

The procedure described for Example 1 was followed except that the polymer utilized was poly(L-lactic acid-)(PLLA) of approximately 2,000 molecular weight (Polysciences), resulting in an intact, highly porous foam which degrades very fast as compared with the polymer of Example 1 due to the low molecular weight of the polymer used.

The procedure as described for Example 1 was followed except that 0.06 grams of the ground PLGA was mixed with 0.02 grams of the gelatin microspheres, resulting in a less porous but stronger polymeric foam, e.g., of approximately 30% porosity.

EXAMPLE 3

PREPARATION OF PLGA/NACL COMPOSITE AND PGA FOAM

The procedure of Example 1 was followed except that sodium chloride particles in the size range of 250–500 μm were utilized, resulting in an intact, highly porous PLGA foam as was prepared in Example 1.

EXAMPLE 4

PREPARATION OF PLLA/NACL COMPOSITE AND PLLA FOAM

The procedure as described for Example 3 was followed except that PLLA of approximately 100,000 molecular weight (Medisorb) was used and the mold was placed in a convection oven at 195° C. for 90 minutes. The higher temperature was required, for example, because homopolymers of high molecular weight such as PLLA form crystallites. Thus the temperature required to cause unhindered flow of the polymeric chains is that in excess of the melting temperature ($T_m$). The melting temperature of PLLA is approximately 180° C. The resultant PLLA foam was similar to that prepared as described in Example 1.

EXAMPLE 5

PREPARATION OF PLLA/PGA COMPOSITE

The procedure as described for Example 4 was followed except that 0.1 gram of ground PLLA and 0.1 gram of PGA fibers of approximately 100 μm diameter and approximately 1 mm length (Ethicon, Summerville, N.J.) were combined. The PGA fibers thus substituted for the NACl particles. PGA fibers have a melting temperature of 230° C. The resulting PLLA/PGA composite had an ultimate porosity capacity of approximately 50%.

EXAMPLE 6

The procedure as described for Example 5 was followed except that 0.1 grams of ground of PLLA of approximately 100,000 molecular weight was combined with 0.1 grams of ground PLLA of approximately 2,000 molecular weight. The resultant $PLLA_{100K}/PLLA_{2K}$ composite had an ultimate porosity capacity of approximately 50%.

EXAMPLE 7

IN VIVO STUDIES

Degradation and creeping substitution studies are performed using the Sprague-Dawley rat proximal tibial model (Gerhart et al., *J. Biomed. Mater. Res.*, 23:1–16, 1988).

In the rat intraosseous medial proximal tibia at a point approximately 2.5 mm caudal to the knee joint, a 2.7 mm hole is drilled. Implants of approximately 2.5 mm×2.5 mm right circular cylindrical are inserted into the drill holes. The contralateral tibial drill hole remains empty as a control.

The compressive strength and modulus of excised implants is measured, for example according to American Society for Testing and Materials (ASTM) Standard 451–86 for bone cements. This consists of compressing the specimen to failure in an Instron 8501 materials testing machine. For example, the compression speed is 1 mm per minute, and the failure load is the load at 2% offset, fracture, or upper yield point, whichever occurs first. The compressive modulus is calculated from the initial linear portion of the load deformation curve.

Biodegradation is analyzed by gel permeation chromatography. In this analysis, the number and weight average of the polymer is measured directly from samples solubilized in chloroform, using a refractive index detector.

Bone ingrowth into the implant is quantitated from histological sections by measuring area fraction of bone with a computerized image analysis system.

The foregoing examples are representative of the features of the claimed invention and are not intended to limit the scope and spirit of the invention as described herein or claimed hereafter.

I claim:

1. A biodegradable, biocompatible prosthetic template comprising:

a biodegradable synthetic polymer matrix; and a pore-creating substance dispersed within said matrix;

wherein said template has a three-dimensional shape and mechanical strength suitable for replacement of load-bearing bone prior to implantation, and wherein said pore creating substance has a biodegradation rate at least about four times greater than the biodegradation rate of the polymeric matrix; and wherein said polymeric matrix is formed of poly(L-lactic-acid) and said pore-creating substance is formed of poly(glycolic acid).

2. A biodegradable, biocompatible prosthetic template comprising:

a biodegradable synthetic polymer matrix; and a pore-creating substance dispersed within said matrix;

wherein said template has a three-dimensional shape and mechanical strength suitable for replacement of load-bearing bone prior to implantation, and wherein said pore creating substance has a biodegradation rate at least about four times greater than the biodegradation rate of the polymeric matrix; and wherein said polymeric matrix is formed of a high molecular weight poly(L-lactic acid) and said pore creating substance is formed of a low molecular weight poly(L-lactic acid).

* * * * *